US012152008B2

(12) United States Patent
Raghavan et al.

(10) Patent No.: US 12,152,008 B2
(45) Date of Patent: Nov. 26, 2024

(54) CYCLOPENTAIMIDAZOLONES FOR THE TREATMENT OF CANCER

(71) Applicants: The Broad Institute, Inc., Cambridge, MA (US); Dana-Farber Cancer Institute, Inc., Boston, MA (US); President and Fellows of Harvard College, Cambridge, MA (US)

(72) Inventors: Srivatsan Raghavan, Boston, MA (US); Bruce Kuan-Yee Hua, Cambridge, MA (US); Shubhroz Gill, Cambridge, MA (US); Stuart Schreiber, Cambridge, MA (US); William Hahn, Boston, MA (US); Paul Clemons, Cambridge, MA (US); Raymond Ng, Boston, MA (US); Partha Nag, Cambridge, MA (US)

(73) Assignees: The Broad Institute, Inc., Cambridge, MA (US); Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 1057 days.

(21) Appl. No.: 17/013,269

(22) Filed: Sep. 4, 2020

(65) Prior Publication Data
US 2020/0399224 A1 Dec. 24, 2020

Related U.S. Application Data

(63) Continuation of application No. PCT/US2019/021003, filed on Mar. 6, 2019.

(60) Provisional application No. 62/639,749, filed on Mar. 7, 2018.

(51) Int. Cl.
C07D 233/32 (2006.01)
A61K 9/00 (2006.01)

(52) U.S. Cl.
CPC .......... *C07D 233/32* (2013.01); *A61K 9/0014* (2013.01); *A61K 9/0019* (2013.01); *A61K 9/0043* (2013.01); *A61K 9/0053* (2013.01)

(58) Field of Classification Search
CPC .................................................. C07D 233/32
See application file for complete search history.

(56) References Cited

U.S. PATENT DOCUMENTS 7,223,759 B2  5/2007 Zhou et al.
2011/0237631 A1  9/2011 Vocadlo et al.

FOREIGN PATENT DOCUMENTS

WO  2013032907 A1  3/2013

OTHER PUBLICATIONS

Registry/Zregistry (CAS Registrysm) Sep. 2016 2 pages.*
Bartlett "Exploiting Chemical Diversity for Drug Discovery" Edited by Paul A Bartlett and Michael Entzeroth, The Royal Society of Chemistry, 2006, pp. 113-118.*
Kim "PubChem in 2021: new data content and improved web interfaces" Nucleic Acids Research, 2021, vol. 49, Database issue Published online Nov. 5, 2020.*
Irwin "Zinc—A Free Database of Commercially Available Compounds for Virtual Screening" J. Chem. Inf. Model. 2005, 45, 177-182.*
"Find ETDs Home > Thesis Resources > Find ETDs" Online: "https://ndltd.org/thesis-resources/find-etds/" Accessed Jan. 31, 2023.*
Gretarsson "Substantial intrinsic variability in chemoradiosensitivity of newly established anaplastic thyroid cancer cell-lines" Acta Oto-Laryngologica 2020, vol. 140, No. 4, 337-343.*
Matthew Daniels "Understanding and reducing variability in cell-based assays." Jan. 18, 2021, Online: "https://www.cellgs.com/blog/understanding-and-reducing-variability-in-cell-based-assays.html" accessed Nov. 3, 2023.*
Hayat, M.A. Autophagy Cancer, Other Pathologies, Inflammation, Immunity, Infection, and Aging vol. 5 Academic Press: Sand Diego, 2015, p. xxi.*
Carlo C. Maley and Mel Greaves Frontiers in Cancer Research Springer: 2016, pp. 18-19.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Ferreira "The Importance of Cancer Cell Lines as in vitro Models in Cancer Methylome Analysis and Anticancer Drugs Testing" Chapter 6 in Oncogenomics and Cancer Proteomics—Novel Approaches in Biomarkers Discovery and Therapeutic Targets in Cancer Intech 2013 pp. 140-166.*
A.M. Bendele "Animal models of rheumatoid arthritis" J Musculoskel Neuron Interact 2001; 1(4):377-385.*
Bendele, "Animal Models of Arthritis: Relevance to Human Disease" Toxicol Pathol 1999 27: 134-142.*

(Continued)

*Primary Examiner* — David K O'Dell
(74) *Attorney, Agent, or Firm* — Greenberg Traurig, LLP; Melissa Hunter-Ensor; Scott Goncher

(57) ABSTRACT

Provided herein are compounds useful for the treatment of various proliferative diseases. These compounds, as well as pharmaceutically acceptable salts thereof may be formulated in pharmaceutical compositions, and may be used in methods of treatment and/or prophylaxis of proliferative diseases, including cancer, and more specifically, pancreatic cancer.

17 Claims, 6 Drawing Sheets

(56) References Cited

OTHER PUBLICATIONS

International Search Report and Written Opinion received in corresponding International Patent Application No. PCT/US2019/021003, mailed May 3, 2019 (12 pages).
Boj et al., "Organoid Models of Human and Mouse Ductal Pancreatic Cancer," Cell, Jan. 15, 2015, vol. 160, pp. 324-338.

* cited by examiner

CYCLOPENTAIMIDAZOLONES FOR THE TREATMENT OF CANCER

CROSS REFERENCE TO RELATED APPLICATIONS

This application is a continuation of and claims priority to International Application No.: PCT/US19/21003, filed Mar. 6, 2019, designating the United States and published in English, which claims the benefit of and priority to U.S. Provisional Application No. 62/639,749, filed Mar. 7, 2018, the entire contents of each of which are incorporated herein by reference.

STATEMENT OF RIGHTS TO INVENTIONS MADE UNDER FEDERALLY SPONSORED RESEARCH

This invention was made with government support under Grant Nos. U01 CA217848, U01 CA176058, U01 CA176152, U54 CA217377, R35 GM127045 and R01 GM038627 awarded by the National Institute of Health, and Grant Nos. DGE1144152 and DGE1745303 awarded by the National Science Foundation. The government has certain rights in the invention.

FIELD OF INVENTION

This invention relates to the treatment and prophylaxis of proliferative diseases involving the administration of novel cyclopentaimidazolones (e.g., tetrahydrocyclopentaimidazolones, hexahydrocyclopentaimidazolones, etc.).

BACKGROUND OF INVENTION

Despite improvements in various proliferative diseases, there remains a critical need to further improve therapies and create targeted therapies for the treatment or prophylaxis thereof. For example, pancreatic ductal adenocarcinoma (PDAC) is a deadly disease with few effective targeted therapies. Pancreatic tumors are notable for having a pronounced stromal response, but the impact of the extracellular matrix (ECM) and tissue architecture on tumor cell behavior and therapeutic response remains unclear. Such biology inhibits the development of therapies for this cancer. Moreover, therapies may prove effective in some cell lines, while having little to no efficacy in others. Thus, there is an urgent need for improvements in, and effective alternatives to, current proliferative disease therapies.

SUMMARY

The present invention relates to novel compounds for the treatment or prophylaxis of a proliferative disease. The compounds may display selective activity against cancer cell lines.

Typically, the anti-cancer compounds have the structure of formula (I)

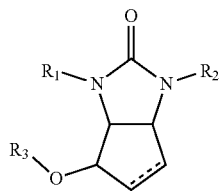

(I)

wherein the "dashed" bond is a single or double bond;
$R_1$ is $C_{1-6}$ alkyl;
$R_2$ is $C_{6-12}$ aryl or $C_{6-13}$ arylalkyl optionally substituted one to three times with halogen, —R, —OR, —(CH$_2$OCH$_2$)$_m$—(CH$_2$)$_p$—N$_3$, —CN, or combinations thereof, wherein "m" and "p" are independently selected at each occurrence from 1-5;
$R_3$ is hydrogen, —(CH$_2$CH$_2$O)$_n$—(CH$_2$)$_p$—N$_3$ or $C_{1-6}$ alkyl; wherein "n" and "p" are independently selected at each occurrence from 1-5;
R is $C_{1-6}$ alkyl;
or a pharmaceutically acceptable salt thereof.

Pharmaceutical compositions for the treatment or prophylaxis of a proliferative disease are also provided comprising a compound having the structure of formula (I) and a pharmaceutically acceptable carrier, excipient, and/or diluent.

Additionally, a method of killing a cancer cell is provided which may comprise contacting said cancer cell with a compound having the structure of formula (I). In most embodiments, the cancer cell is in vitro or in vivo.

A method of treatment or prophylaxis of a proliferative disease is also provided comprising administering an effective amount of a compound having the structure of formula (I) to a patient in need thereof.

DETAILED DESCRIPTION

Definitions

Figure 1:
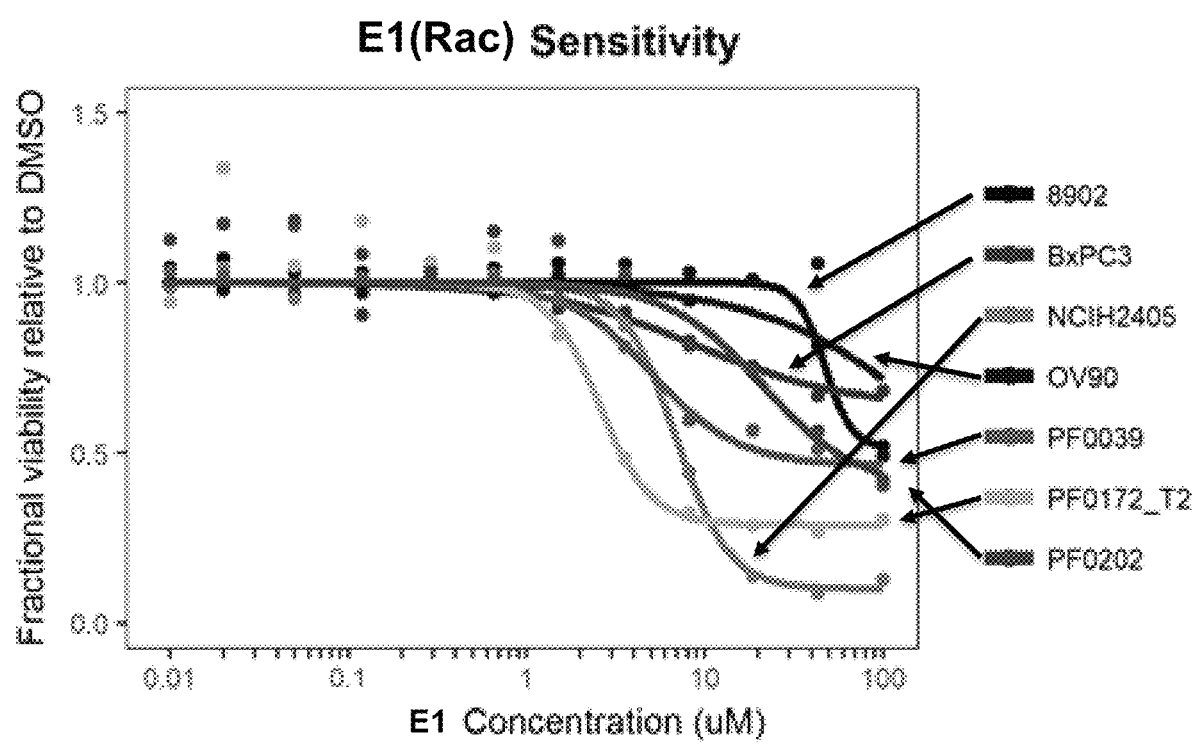
FIG. 1 shows the viability of different patient-derived organoids (identified as PF0039, PF0172_T2, and PF0202) and cancer cell lines (8902, BxPC3, NCIH2405, and OV90) with respect to E1 illustrating the different effect E1 may have on different organoids and cell lines.

It is to be understood that the terminology employed herein is for the purpose of describing particular embodiments, and is not intended to be limiting. Further, although any methods and materials similar or equivalent to those described herein can be used in the practice or testing of the disclosure, the preferred methods and materials are now described.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

As used herein, the term "alkyl," alone or in combination with other groups, refers to a branched or straight-chain monovalent saturated aliphatic hydrocarbon radical of one to twenty carbon atoms (e.g., one to sixteen carbon atoms, one to twelve carbon atoms, one to ten carbon atoms, or one to six carbon atoms, etc.). In some embodiments, the alkylene can be further substituted with 1, 2, 3, or 4 substituent groups as defined herein.

The term "alkylene" as used herein, represents a saturated divalent hydrocarbon group derived from a straight or branched chain saturated hydrocarbon by the removal of two hydrogen atoms, and is exemplified by methylene, ethylene, and isopropylene. In some embodiments, the alkylene can be further substituted with 1, 2, 3, or 4 substituent groups as defined herein.

The term "aryl" refers to an aromatic mono- or polycyclic radical of 6 to 12 carbon atoms having at least one aromatic ring. Examples of such groups include, but are not limited to, phenyl, naphthyl, 1,2,3,4-tetrahydronaphthalyl, 1,2-dihydronaphthalyl, indanyl, and 1H-indenyl. In some embodiments, the alkylene can be further substituted with 1, 2, 3, or 4 substituent groups as defined herein.

The "arylalkyl" group, as used herein, represents an aryl group, as defined herein, attached to the parent molecular group through an alkylene group. Exemplary unsubstituted arylalkyl groups are from 7 to 30 carbons (e.g., from 7 to 16 or from 7 to 20 carbons, such as $C_{6-10}$ aryl $C_{1-6}$ alkyl, $C_{6-10}$ aryl $C_{1-10}$ alkyl, or $C_{6-10}$ aryl $C_{1-20}$ alkyl). In some embodiments, the alkylene and the aryl each can be further substituted with 1, 2, 3, or 4 substituent groups as defined herein for the respective groups.

A "substituted" hydrocarbon may have as a substituent one or more hydrocarbon radicals, substituted hydrocarbon radicals, or may comprise one or more heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (e.g., F, Cl, Br, I, etc.), boron, silicon, etc. In some embodiments, heteroatoms will be selected from the group consisting of oxygen, nitrogen, sulfur, phosphorous, and halogen (e.g., F, Cl, Br, I, etc.). In some embodiments, a heteroatom or group may substitute a carbon. In some embodiments, a heteroatom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo", replacing a hydrogen in the backbone or chain, etc.).

Substituents may refer to a group substituted on a hydrocarbon (e.g., an alkyl, haloalkyl, cycloalkyl, heterocyclyl, heterocycloalkenyl, cycloalkenyl, aryl, heteroaryl group, etc.) at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo (e.g., —F, —Cl, etc.), $C_{1-12}$ straight chain or branched chain alkyl, $C_{2-12}$ alkenyl, $C_{2-12}$ alkynyl, $C_{3-12}$ cycloalkyl, $C_{6-12}$ aryl, $C_{3-12}$ heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Unless otherwise noted, all groups described herein optionally contain one or more common substituents, to the extent permitted by valency. It is understood by one of ordinary skill in the chemistry art that substitution at a given atom is limited by valency. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable.

Compounds provided herein can have one or more asymmetric carbon atoms and can exist in the form of optically pure enantiomers, mixtures of enantiomers such as racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as chiral chromatography and separation methods based thereon. The appropriate technique and/or method for separating an enantiomer of a compound described herein from a racemic mixture can be readily determined by those of skill in the art.

By "proliferative disease" is meant a disease that is caused by or results in inappropriately high levels of cell division, inappropriately low levels of apoptosis, or both. For example, cancer is an example of a proliferative disease.

"Racemate" or "racemic mixture" means a mixture containing two enantiomers, wherein such mixtures exhibit no optical activity; i.e., they do not rotate the plane of polarized light. "Geometric isomer" means isomers that differ in the orientation of substituent atoms (e.g., to a carbon-carbon double bond, to a cycloalkyl ring, to a bridged bicyclic system, etc.). Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds disclosed herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer may be at least 50%, 60%, 70%, 80%, 90%, 99%, or 99.9% by weight relative to the other stereoisomers. When a single enantiomer is named or depicted by structure, the depicted or named enantiomer may be at least 50%, 60%, 70%, 80%, 90%, 99%, or 99.9% by weight optically pure. When a single diastereomer is named or depicted by structure, the depicted or named diastereomer may be at least 50%, 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer may be at least 50%, 60%, 70%, 80%, 90%, 99%, or 99.9% by mole fraction pure relative to the other stereoisomers. When a single enantiomer is named or depicted by structure, the depicted or named enantiomer may be at least 50%, 60%, 70%, 80%, 90%, 99%, or 99.9% by mole fraction pure. When a single diastereomer is named or depicted by structure, the depicted or named diastereomer may be at least 50%, 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The disclosure embraces all of these forms.

The term "effective amount" or "therapeutically effective amount" of an agent, as used herein, is that amount sufficient to effect beneficial or desired results, such as clinical results, and, as such, an "effective amount" depends upon the context in which it is being applied. For example, in the context of administering an agent that is an anti-cancer agent, an effective amount of an agent is, for example, an amount sufficient to achieve alleviation or amelioration or prevention or prophylaxis of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable, as compared to the response obtained without administration of the agent.

As used herein, and as well understood in the art, "to treat" a condition or "treatment" of the condition (e.g., the conditions described herein such as cancer) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

Useful pharmaceutical carriers for the preparation of the compositions hereof, can be solids, liquids, or gases. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the term "pharmaceutically acceptable salt" refers to salts of any of the compounds described herein that within the scope of sound medical judgment, are suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxyethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

By "reference" is meant a standard or control condition.

By "selective inhibitors of protein kinase mitogen-activated agents" also known as "MEK inhibitor" in the present invention, reference is made to selective inhibitors of an activated protein kinase by mitogens such as kinases MEK1 and/or MEK2 e.g. trametinib, selumetinib, binimetinib, or cobimetinib.

As used herein, the term "subject" refers to any organism to which a composition in accordance with the disclosure may be administered, e.g., for experimental, diagnostic, prophylactic, and/or therapeutic purposes. Typical subjects include any animal (e.g., mammals such as mice, rats, rabbits, non-human primates, and humans, etc.). animals in the family Muridae (e.g., rats, mice, etc.). A subject may seek or be in need of treatment, require treatment, be receiving treatment, may be receiving treatment in the future, or a human or animal that is under care by a trained professional for a particular disease or condition.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gel cap, and syrup.

Other features and advantages of the disclosure are described in the following detailed description, the drawings, and the claims.

Compounds of the Invention

The present disclosure provides for novel compounds and pharmaceutical compositions useful for the treatment or prophylaxis of a proliferative disease. The disclosure also provides methods of using these compounds and compositions.

The anti-cancer compounds may have the structure of formula (I)

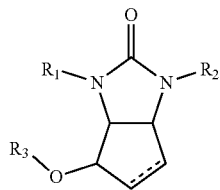
(I)

wherein the "dashed" bond is a single or double bond;
$R_1$ is $C_{1-6}$ alkyl;
$R_2$ is $C_{6-12}$ aryl or $C_{7-13}$ arylalkyl optionally substituted one to three times with halogen, —R, —OR, —(CH$_2$OCH$_2$)$_m$—(CH$_2$)$_p$—N$_3$, —CN, or combinations thereof, wherein "m" and "p" are independently selected at each occurrence from 1-5;
$R_3$ is hydrogen, —(CH$_2$CH$_2$O)$_n$—(CH$_2$)$_p$—N$_3$ or $C_{1-6}$ alkyl; wherein "n" and "p" are independently selected at each occurrence from 1-5;
R is $C_{1-6}$ alkyl;
or a pharmaceutically acceptable salt thereof.

In some embodiments, the compound may have the structure of formula (Ia), (Ib), (Ic), and/or (Id):

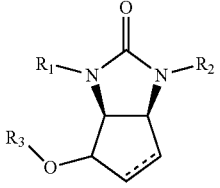
(Ia)

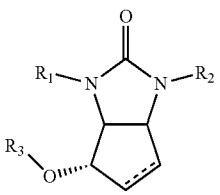
(Ib)

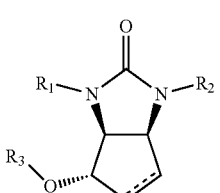
(Ic)

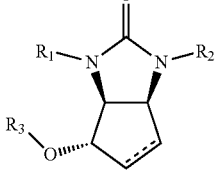
(Id)

In some embodiments, the compound according $R_1$ is $C_4$ alkyl (e.g., isobutyl, etc.). In some embodiments, $R_2$ is phenyl or benzyl. $R_2$ may be optionally substituted once with —F, —Cl, —CN, —CH$_3$, or —OCH$_3$. In preferred embodiments, $R_2$ is unsubstituted phenyl, para-substituted phenyl, or meta-substituted phenyl. In some embodiments, $R_2$ is benzyl (e.g., substituted or unsubstitued). $R_3$ may be hydrogen or lower alkyl (e.g., methyl, ethyl, etc.). Typically, the "dashed" bond is a double bond. In other embodiments, the "dashed" bond is a single bond.

In some embodiments, the compound is a racemic mixture, a substantially pure enantiomer, a mixture of enantiomers, or a mixture of diastereoisomers. For example, the compound may be a racemic mixture, substantially pure enantiomer, or a mixture of enantiomers of compounds having the structure of formula (Ic) and (Id):

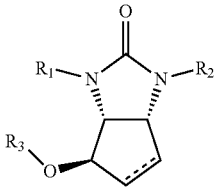
(Ic)

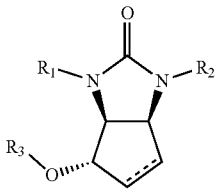
(Id)

In some embodiments, the compound is selected from:

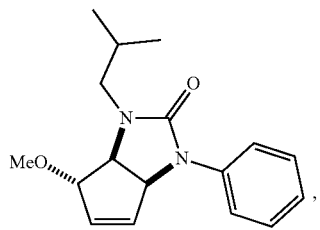
E1(c)

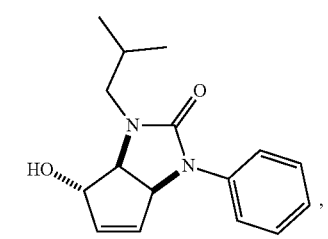
E2(c)
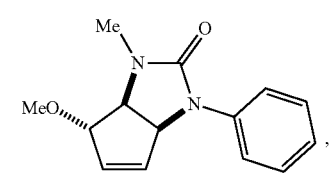
E3(c)
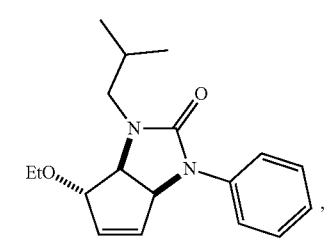
E4(c)
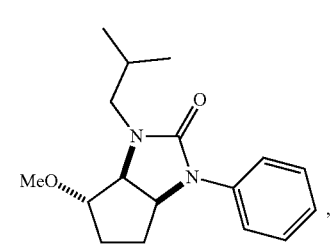
E5(c)
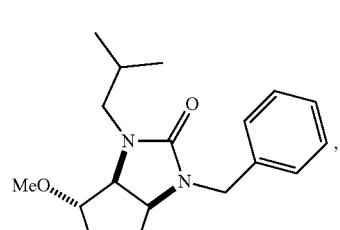
E6(c)
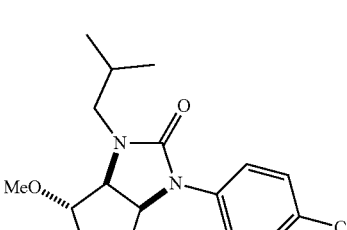
E7(c)
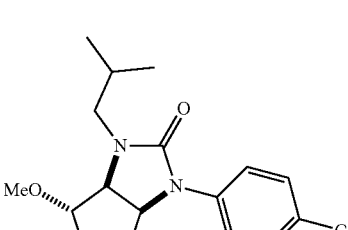
E8(c)
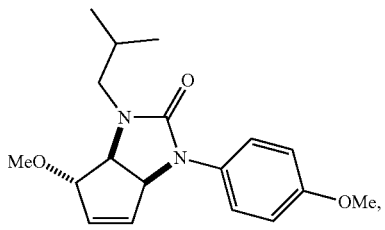
E9(c)
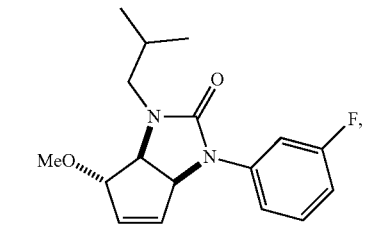
E10
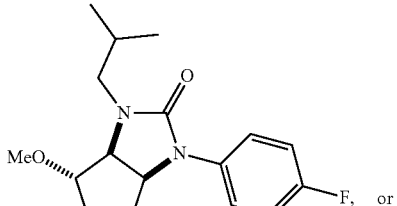
E11
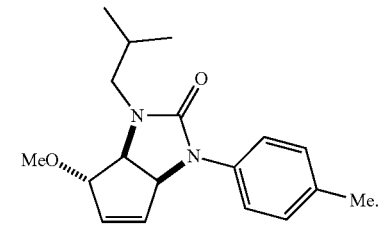
, or
E12
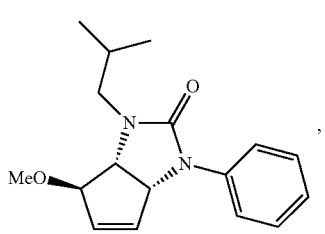
In some embodiments, the compound is selected from:
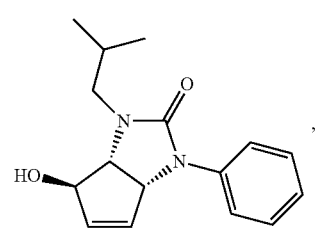
E1(d)
E2(d)

E3(d)
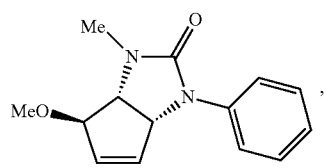

E4(d)
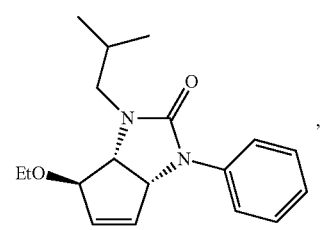

E5(d)
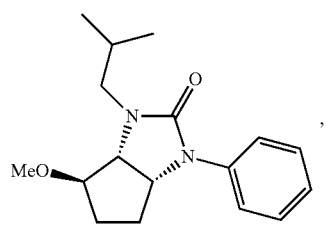

E6(d)
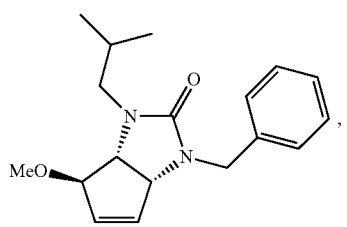

E7(d)
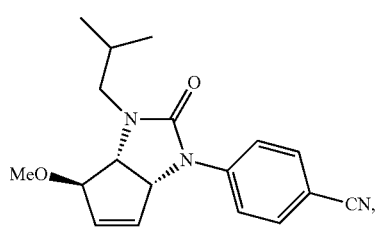

E8(d)
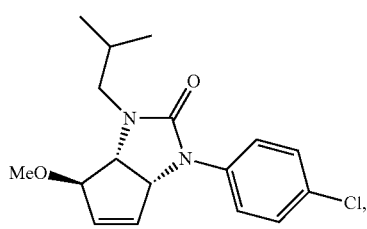

E9(d)
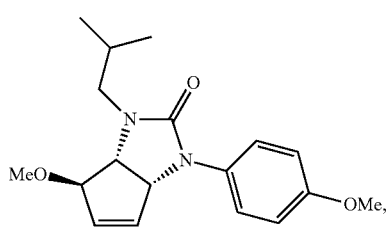

E10(d)
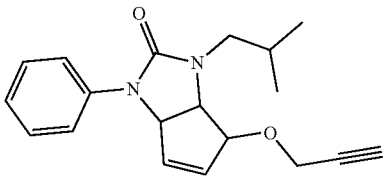

E11(d)
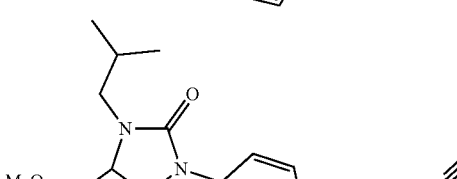

E12(d)
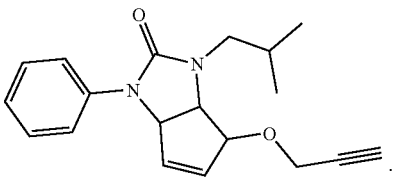

or racemic mixtures thereof.

In some embodiments the compound may be comprise a linker group suitable for conjugation to another molecule. For example, in some embodiments, the compound comprises an azido containing moiety such as —(CH$_2$OCH$_2$)$_m$—(CH$_2$)$_p$—N$_3$, —(CH$_2$CH$_2$O)$_n$—(CH$_2$)$_p$—N$_3$, wherein m and p are independently selected at each occurrence from 0-5 (e.g., zero, one, two, three, four, five). In some embodiments, the compound has the structure:

In certain implementations, the compound has the structure:

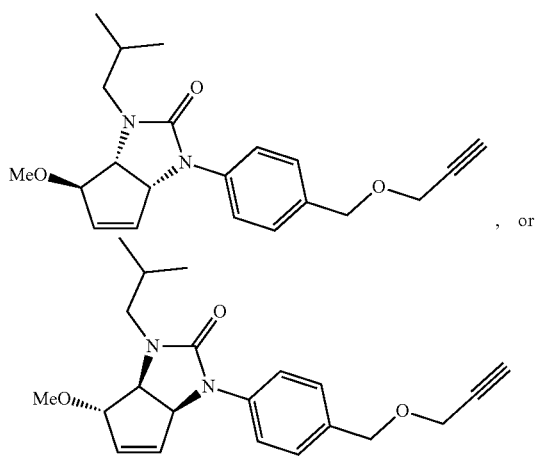

, or or racemic mixtures thereof.

The compounds of the present invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present invention and their pharmaceutically acceptable acid addition salts. Salts derived from appropriate bases include alkali metal (e.g., sodium), alkaline earth metal (e.g., magnesium), ammonium and N-(alkyl)$_4^+$-salts. The present invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the present invention.

The present invention also includes various hydrate and solvate forms of the compounds.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Pharmaceutical Compositions

1. Formulations

For use in the methods described herein, the compounds having the structure of formula (I) can be formulated in pharmaceutical compositions. The formulation selected can vary depending on the subject to be treated, the mode of administration, and the type of treatment desired (e.g., prevention, prophylaxis, or therapy). A summary of formulation techniques is found in *Remington: The Science and Practice of Pharmacy*, 21$^{st}$ *Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference. Exemplary routes of administration and formulations are described as follows.

In the practice of the disclosed methods, the compounds (or pharmaceutically acceptable salts thereof) or compositions can be administered by any of the usual and acceptable routes and methods known in the art. The compounds or compositions can thus be administered, for example, by the enteral or gastrointestinal route (e.g., orally or rectally), topically (e.g., to the skin or an accessible mucous membrane (e.g., an intraoral (e.g., sublingual or buccal), intranasal, intrarectal, or genitourinary surface), parenterally (e.g., by intramuscular, intravenous, subcutaneous, intraarticular, intravesicular, intraperitoneal, intrathecal, epidural, ocular, or aural application or injection), transdermally, or by inhalation (e.g., by aerosol).

The compositions can be in the form of a solid, liquid, or gas, as determined to be appropriate by those of skill in the art. Thus, as general examples, the pharmaceutical compositions may be in the form of tablets, capsules, syrups, pills, enterically coated or other protected formulations, sustained release formulations, elixirs, powders, granulates, suspensions, emulsions, solutions, gels (e.g., hydrogels), pastes, ointments, creams, plasters, transdermal patches, drenches, suppositories, enemas, injectables, implants, sprays, or aerosols.

The compositions, in general, include an effective amount of a compound described herein and one or more pharmaceutically acceptable carriers or excipients, as is well known in the art. The compositions can thus include one or more diluents, buffers, preservatives, salts, carbohydrates, amino acids, carrier proteins, fatty acids, lipids, etc. The compounds described herein may be present in amounts totaling, for example, 0.1-95% by weight of the total weight of the composition. In some embodiments, the composition comprises from 0.1% to 20% or 20% to 40% or 40% to 60% or 60% to 80% of the anti-cancer compound having the structure of formula (I) by weight of the composition.

For injection, formulations can be prepared in conventional forms as liquid solutions or suspensions, or as solid forms suitable for solution or suspension in liquid prior to injection, or as emulsions. Suitable excipients for these formulations include, for example, water, saline, dextrose, and glycerol. Such compositions can also contain nontoxic auxiliary substances, such as wetting or emulsifying agents, and pH buffering agents, such as sodium acetate, sorbitan monolaurate, and so forth.

Formulations for oral use include tablets containing a compound in a mixture with one or more non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, and buffering agents.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

2. Kits

The compounds and compositions can be packaged in a kit, optionally with one or more other pharmaceutical agents. Non-limiting examples of the kits include those that contain, e.g., two or more pills, a pill and a powder, a suppository and a liquid in a vial, or two topical creams. The kits can include optional components that aid in the administration of the unit dose to subjects, such as vials for reconstituting powder forms, syringes for injection, customized IV delivery systems, or inhalers. Additionally, the unit dose kits can contain instructions for preparation and administration of the compositions. The kits can be manufactured as a single use unit dose for one subject, multiple uses for a particular subject (at a constant dose or in which the individual compounds may vary in potency as therapy progresses); or the kits can contain multiple doses suitable for administration to multiple subjects ("bulk packaging"). The kit components can be assembled in cartons, blister packs, bottles, and tubes.

3. Dosage

The dose of a compound depends on a number of factors, such as the manner of administration, the age and the body weight of the subject, and the condition of the subject to be treated, and ultimately will be decided by the attending physician. Such an amount of the compound, as determined by the attending physician or veterinarian, is referred to herein, and in the claims, as a "therapeutically effective amount." For example, the dose of a compound disclosed herein is typically in the range of 1 to 1000 mg per day. Preferably, the therapeutically effective amount is in an amount of from 1 mg to 500 mg per day.

Administration of each drug, as described herein, can, independently, be one to four times daily for one day to one year, and may even be for the life of the subject. Chronic, long-term administration may be indicated.

4. Combination Therapies

The compounds and pharmaceutical compositions can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

In some embodiments, anti-cancer compounds having the structure of formula (I) are coadministered with other anti-cancer agents. Examples of other anti-cancer agents to combine with the compounds described herein include pharmaceuticals for the treatment of a proliferative disease (e.g., MEK inhibitors including trametinib, cobimetinib, or binimetinib, B-Raf inhibitors including vemurafenib, etc.). Other examples of drugs to combine with the compounds described herein include pharmaceuticals for the treatment of different, yet associated or related symptoms or indications. Combination methods can involve the use of the two (or more) agents formulated together or separately, as determined to be appropriate by those of skill in the art. In one example, two or more drugs are formulated together for the simultaneous or near simultaneous administration of the agents.

When the compositions of the present disclosure include a combination of a compound of formula (I) described herein and one or more additional therapeutic or prophylactic agents, both the compound and the additional agent can be present at dosage levels of between 1 to 100%, and more preferably between 5 to 95% of the dosage normally administered in a monotherapy regimen.

Methods

Also provided herein is a method for the treatment or prophylaxis of one or more proliferative diseases comprising administering to a subject in need thereof an effective amount of a compound having the structure of formula (I). In some embodiments, the treatment results in the sustained response in the individual following cessation of treatment. In certain implementations, the proliferative disease is cancer. In some embodiments, the cancer cell of the cancer is from the cell line 8902, BxPC3, NCIH2405, or OV90. In certain embodiments, the compound has an $EC_{50}$ in the cancer cells of less than 10 µM.

In embodiments, the one or more proliferative diseases, disorders, or conditions can be cancer, including but not limited to neoplasm or malignant tumors found in mammals (e.g., humans), including leukemia, carcinomas, and sarcomas. Exemplary cancers that may be treated with a compound or method provided herein include cancer of the thyroid, endocrine system, brain, breast, cervix, colon, head and neck, liver, kidney, lung, non-small cell lung, melanoma, mesothelioma, ovary, sarcoma, stomach, uterus, medulloblastoma, colorectal cancer, or pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, pancreatic ductal adenocarcinoma, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In some embodiments, the cancer is melanoma, gastrointestinal stromal tumors, lung cancer, skin cancer, colorectal cancer, breast cancer, prostate cancer, pancreatic ductal adenocarcinoma, ovarian cancer, thyroid cancer, hematological malignancy, papillary thyroid carcinoma, cholangiocarcinoma, metastatic melanoma, glioblastoma multiform, or acute myelogenous leukemia.

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally, or by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from 0.01 mg/kg to 1000 mg/kg (e.g., from 0.01 to 100 mg/kg, from 0.1 to 100 mg/kg, from 1 to 100 mg/kg, from 1 to 10 mg/kg), every 4 to 120 hours, or according to the requirements of the particular drug. In some embodiments, compounds having the structure of formula (I) may be administered intravenously, intramuscularly, subcutaneously, topically, orally, intraperitoneally, intraorbitally, by implantation, by inhalation, intrathecally, intraventricularly, or intranasally. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, New York, 537 (1970). In certain embodiments, the compositions are administered by oral administration or administration by injection. The methods herein contemplate administration of an effective amount of compound or compound composition to achieve the desired or stated effect. Typically, the pharmaceutical compositions of the present disclosure will be administered from 1 to 6 times per day or, alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of the present disclosure may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In some embodiments, the compounds described herein can be coadministered with one or more other therapeutic agents. In certain embodiments, the additional agents may be administered separately, as part of a multiple dose regimen, from the compounds of the present disclosure (e.g., sequentially, on different overlapping schedules with the administration of one or more compounds of formula (I) (including any subgenera or specific compounds thereof). In other embodiments, these agents may be part of a single dosage form, mixed together with the compounds of the present disclosure in a single composition. The other therapeutic agent may be, for example, vemurafenib or a pharmaceutically acceptable salt thereof. In some embodiments, the other therapeutic agent may be a MEK inhibitor (e.g., trametinib, cobimetinib, binimetinib).

A method killing a cancer cell is also provided comprising contacting a cancer cell with a compound having the structure of formula (I). In some embodiments, the cancer cell is in vitro or in vivo. In some embodiments, the cancer is from several cell lines including PaTu 8902, BxPC-3, NCIH2405, OV-90, PF0039, PF0172-T2, or PF0202. In some embodiments, the compound has increased bioactivity (e.g., lower $IC_{50}$ value) for the cell line as compared to the compound in other cancer cell lines.

EXAMPLES

The following Examples illustrate the synthesis and biological measurements of a representative number of anticancer compounds. Accordingly, the Examples are intended to illustrate but not to limit the disclosure. Additional compounds not specifically exemplified may be synthesized using conventional methods in combination with the methods described herein.

Example 1: Chemical Synthesis

Shown below are non-limiting synthetic schemes which may be used to prepare selected, non-limiting examples of compounds of the invention from commercially available starting materials.

A general synthetic scheme for compounds having the structure of Formula I is shown below.

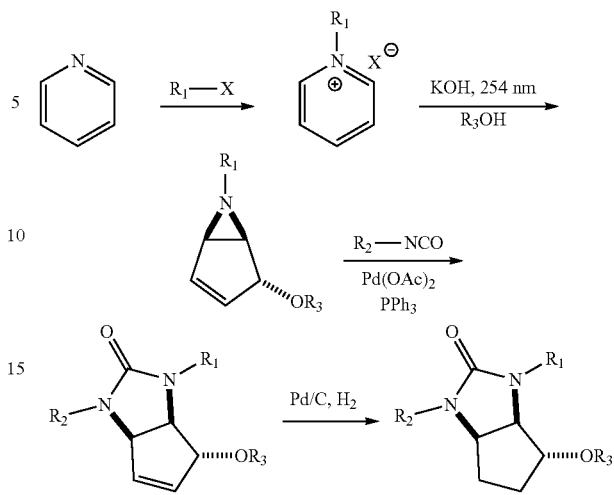

Compounds with the "dashed" bond as a single bond (e.g., compound E5, etc.) may be synthesized with the final hydrogenation step. Those compounds where the "dashed" bond as a double bond (e.g., E1, E2, E3, etc.) do not require this final hydrogenation step. Individual steps of the reaction schema shown below may proceed as disclosed in Kaplan, L., et al., *J. Am. Chem. Soc.* 94: 3283 (1972) Butler, et al., *J. Org. Chem.* 65: 5887 (2000) and/or Trost, B., et al., *J. Am. Chem. Soc.* 125: 11836 (2003), each hereby incorporated by reference in their entirety.

Example 2: Chemical Synthesis of E1 and Enantiomers Thereof

E1 as a racemic mixture (E1(Rac)), and two enantiopurified mixtures E1 (synthesized with (S,S)-5 reagent or (R,R)-5 reagent) were synthesized as shown below. The stereochemistry indicated for the inventive compounds in these schemas reflects the relative configuration of the chiral centers and not absolute stereochemistries. E1 as a racemic mixture (E1(Rac)), and two enantiopurified mixtures E1 (synthesized with (S,S)-5 reagent labeled as E1(S,S) or (R,R)-5 reagent labeled as E1(R,R)) were synthesized using these schema. It will be understood that (R,R)-5 is not required to synthesize E1(c) (or E2(c)-E12(c)) or that (S,S)-5 is required to synthesize E1(d) (or E2(d)-E12(d)). However, in some embodiments, E1(c)-E12(c) may be defined by the dominant enantiomer produced using (R,R)-5 as a reagent. Additionally, E1(d)-E12(d) may be defined by the dominant enantiomer produced using (S,S)-5 as a reagent. In the synthesis described below, the ratio of enantiomers produced using (R,R)-5 was 85:15 by weight (70% ee) and 15:85 by weight when using (S,S)-5.

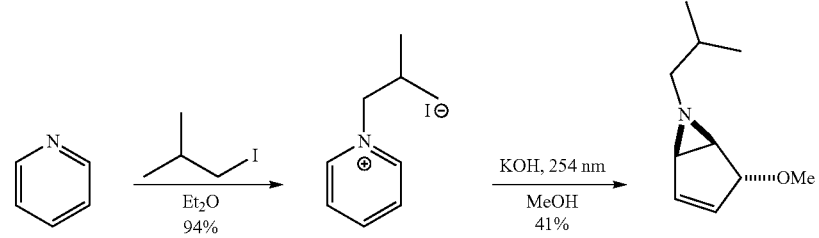

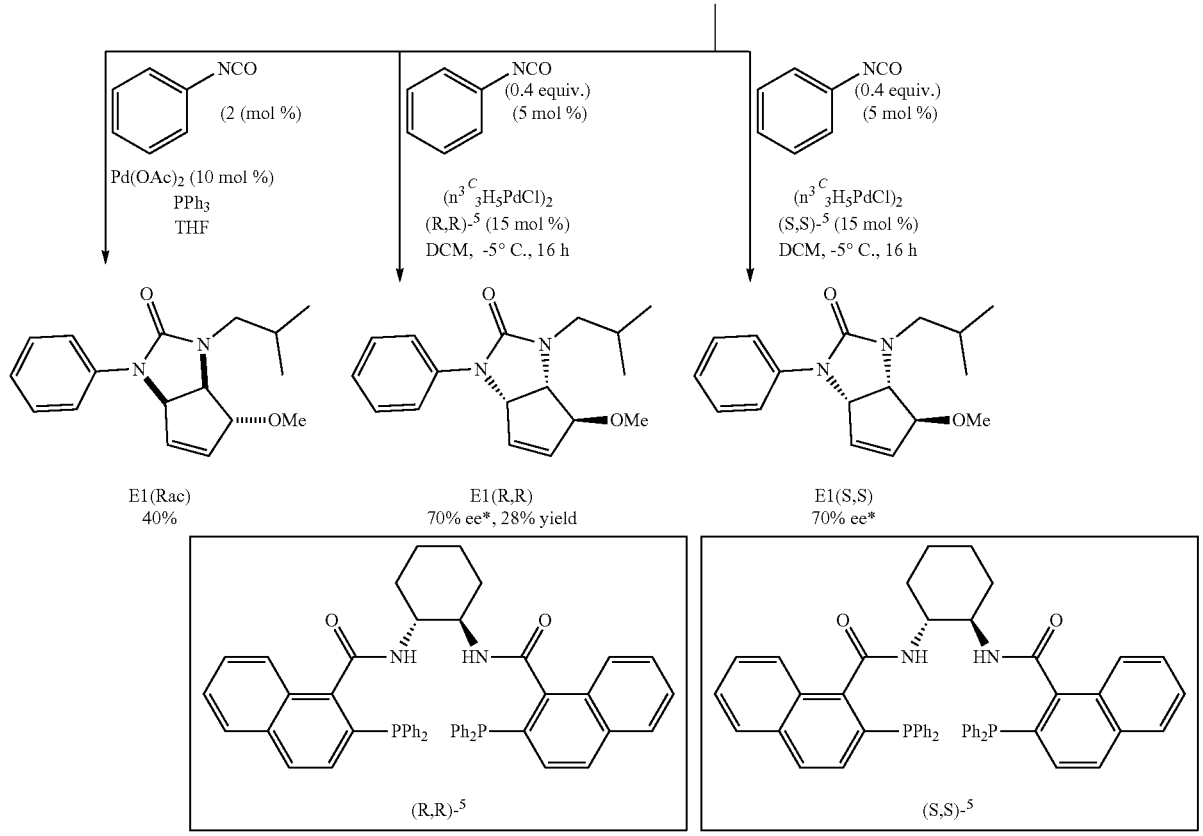

Example 3: Organoid and Cell Line Screens

Figure 2A:
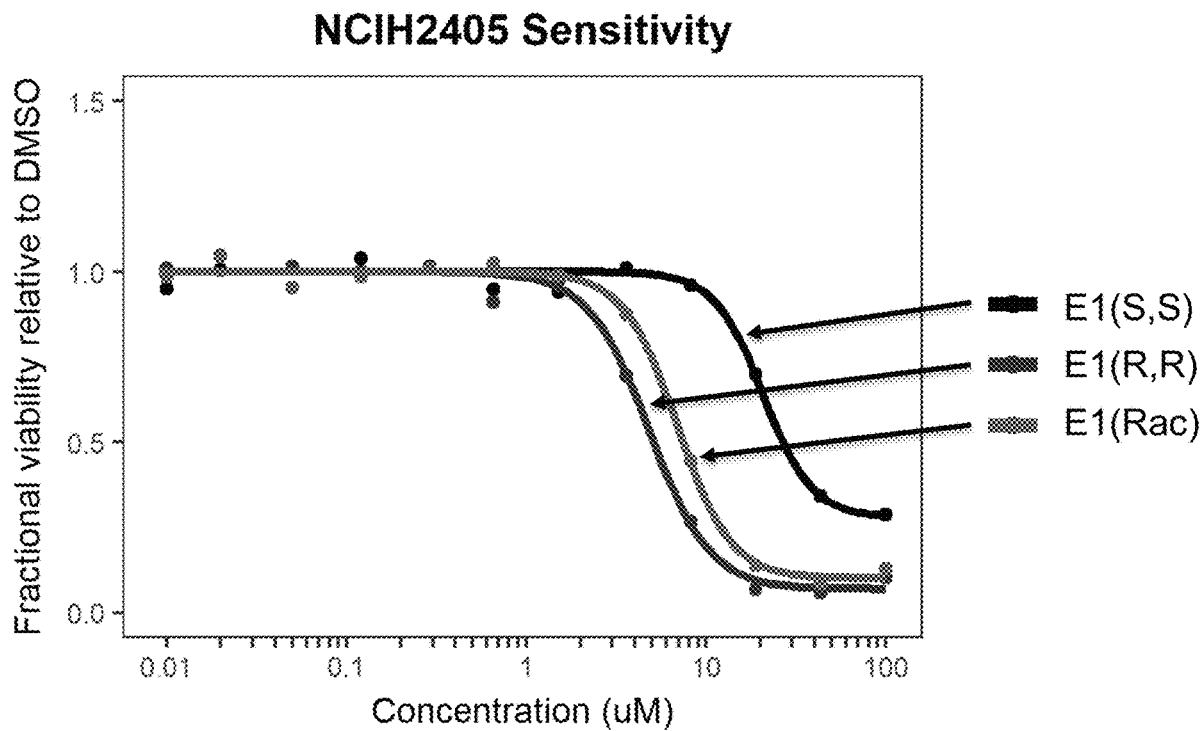
FIG. 2A shows the viability of the NCIH2405 cell line with respect to various enantiomers and racemic mixtures of E1.
Figure 2B:
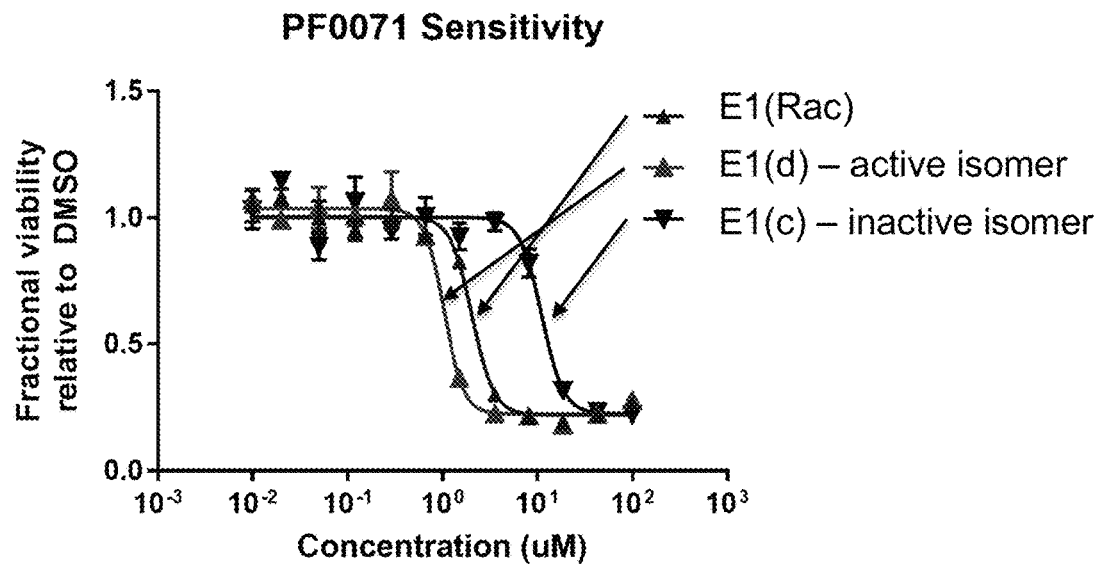
FIG. 2B shows the viability of the PF0071 organoid with respect to various enantiomers and racemic mixtures of E1. The active and inactive enantiomers are identified by their absolute structures as determined by X-ray crystallography following enantio-purification of E1(Rac).

Compounds were tested on patient-derived tumor organoids. Such organoids retain the three-dimensional structure of the tissue providing conditions that are more representative of in vivo behavior. Such organoids are described by Boj, Sylvia, et al., *Cell* 160: 324 (2015), hereby incorporated by reference in its entirety. Briefly, cultures of primary and metastatic pancreatic tumor specimens as patient-derived xenografts, 3D tumor organoids, and patient-derived cell lines were produced including a cohort of 21 patient-derived xenografts and 67 organoid cultures from primary and metastatic pancreatic tumor specimens. The functional dependencies of compounds in these patient-derived samples were measured on a 3D organoid and its matched 2D patient-derived cell lines. Conditions were optimized for performing high-throughput compound screening of 3D organoids, including suspension culture with Matrigel in 384-well plates, viability assessment with CellTiter-Glo 3D. FIG. 1 shows the measured fractional organoid viability of Compound E1 as a function of E1 concentration in patient derived organoids (identified as PF0039, PF0071, PF0172-T2, and PF0202) and from several cell lines including PaTu 8902, BxPC-3, NCIH2405, and OV-90. As can be seen, Compound E1 was shown to have a dose-dependent effect on only a subset of organoids, suggesting some degree of target specificity (FIG. 1). FIG. 2A illustrates the dose dependent responses of an enantioenriched sample of Compound E1 synthesized using an enantio-purified sample of E1 in the (R,R)-configuration (70% ee) (e.g., E1(R,R)), an enantioenriched sample of E1 ("E1(S,S)"), and racemic mixtures of E1 on NCIH2405 cells ("E1"). As can be seen, the enantiomers have different activities on NCIH2405 cells. Similarly, FIG. 2B illustrates the dose dependent responses of the racemate and enantio-purified samples (enantio-purified from E1(Rac)) of various purities on PF0071 organoids with identification of the active and inactive racemates. In FIG. 2B, the active and inactive isomers are identified by their actual configurations. The actual configuration of the active and inactive isomer was determined by X-ray crystallography as described in Example 3 following enantio-purification of the racemic mixture.

Table 1 gives the IC$_{50}$ values (µM) of compounds having the structure of formula (I) (including E1(S,S) and E1(Rac) in patient-derived organoids and several cell lines. Compounds E1-E12 were synthesized as described above as racemates (i.e., E1(Rac)-R12(Rac), and E1(S,S) and E1(R,R) were synthesized using the (S,S)-5 reagent or (R,R)-5 reagent, respectively, as described above.

TABLE 1

| Cmp | $R_1$ | $R_3$ | $R_2$ | 8902 | BxPC3 | NCIH 2405 | OV90 | PF 0039 | PF 0172_T2 | PF 0202 |
|---|---|---|---|---|---|---|---|---|---|---|
| E1 | iBu | Me | phenyl | >100 | >100 | 7.41 | >100 | 22.3 | 3.41 | 55.4 |
| E1(S,S) | iBu | Me | phenyl | >100 | >100 | 26.8 | >100 | 34.8 | 11.2 | >100 |

TABLE 1-continued

| Cmp | $R_1$ | $R_3$ | $R_2$ | 8902 | BxPC3 | NCIH 2405 | OV90 | PF 0039 | PF 0172_T2 | PF 0202 |
|---|---|---|---|---|---|---|---|---|---|---|
| E1(R,R) | iBu | Me | phenyl | >100 | >100 | 5.08 | >100 | >100 | 3.25 | 63.9 |
| E10(Rac) | iBu | Me | 3-fluorophenyl | >100 | 66.6 | 3.44 | 83.9 | 8.14 | 2.22 | 36.9 |
| E11(Rac) | iBu | Me | 4-fluorophenyl | >100 | >100 | 10.2 | 93.6 | 28.2 | 4.08 | 49.5 |
| E12(Rac) | iBu | Me | p-tolyl | >100 | >100 | 2.04 | 85.9 | 7.42 | 1.21 | 51.4 |
| E8(Rac) | iBu | Me | 4-chlorophenyl | 33.9 | 17.3 | 2.58 | 30.7 | 8.19 | 2.15 | 27.9 |
| E7(Rac) | iBu | Me | 4-cyanophenyl | 75.1 | >100 | >100 | >100 | >100 | >100 | 100 |
| E3(Rac) | Me | Me | phenyl | >100 | >100 | >100 | >100 | >100 | 85.8 | >100 |
| E2(Rac) | iBu | H | phenyl | >100 | >100 | >100 | >100 | 31.7 | 4.05 | >100 |
| E4(Rac) | iBu | Et | phenyl | >100 | 96.4 | 14.3 | 76.9 | 25.8 | 3.4 | 40.2 |
| E5(Rac) | iBu | Me | phenyl | >100 | 64.4 | 4.11 | 83.3 | 7.26 | 1.16 | 16.5 |
| E6(Rac) | iBu | Me | benzyl | >100 | >100 | >100 | 96.4 | 40.7 | 17.4 | 65.3 |
| E9(Rac) | iBu | Me | 4-methoxyphenyl | 76.8 | 56.4 | 58.8 | 65.5 | 43.5 | 88.6 | 47.1 |

Example 4: Identification of Active and Inactive Enantiomers

E1(Rac), E5(Rac), and E8(Rac) were synthesized as racemic mixtures (i.e., without a chiral catalyst) and separated into six optically pure compounds. The PF0071 sensitivity screen was performed on each of these six enantiopure compounds to identify three active compounds and three inactive compounds (see, e.g., FIG. 2, FIG. 3) for this cell line.

Four of these optically pure compounds were crystalized to identify the exact stereochemistry with crystallography. Crystals were mounted on a diffractometer and crystallographic data was collected at 100 K. The intensities of the reflections were collected by means of a Bruker APEX DUO CCD diffractometer ($CU_{K\alpha}$ radiation, $\lambda=1.54178$ Å) equipped with an Oxford Cryosystems nitrogen flow apparatus. The collection method involved 1.0° scans in ω at −30°, −55°, −80°, 30°, 55°, 80° and 115° in 2θ. Data integration down to 0.84 Å resolution was carried out using SAINT V8.37 A (Bruker diffractometer, 2015) with reflection spot size optimization. Absorption corrections were made with the program SADABS (Bruker diffractometer, 2015). The molecular structure was solved by the Intrinsic Phasing methods and refined by least-squares methods again $F^2$ using SHELXT-2014 (Sheldrick, 2015) and SHELXL-2014 (Sheldrick, 2015) with OLEX 2 interface (Dolomanov, et al., 2009). In the analysis, non-hydrogen atoms were refined anisotropically, and hydrogen atom positions were assumed based on those non-hydrogen atoms. The Ortep plots produced with SHELXL-2014 program, and the other drawings were produced with Accelrys DS Visualizer 2.0 (Accelrys, 2007). The computer programs SAINT 8.37A (Bruker-AXS, 2015), SHELXT2014 (Sheldrick, 2015), SHELXL2014 (Sheldrick, 2015), Bruker SHELXTL (Sheldrick, 2015) were used to analyse the crystallographic data to elucidate the chemical structures as identified in Table 2.

With the absolute stereochemistry identified, the correlation between specific isomer and activity was determined for PF0071 organoids. Table 2 compares the activities of each set of racemates that were measured as compared to the designations illustrated in FIG. 2B. For each enantiomeric pair, the analog typically with the lower $IC_{50}$ value was identified as "active" and the analog with the higher $IC_{50}$ value was identified as "inactive." Typically, each inactive enantiomer had an $IC_{50}$ value more than 10× greater than the active enantiomer.

TABLE 2

| Compound Structure | Activity (active or inactive) |
|---|---|
| E5(d) | Active |
| E5(c) | Inactive |
| E1(d) | Active |
| E1(c) | Inactive |

TABLE 2-continued

| Compound Structure | Activity (active or inactive) |
|---|---|
| E8(d) | Active |
| E8(c) | Inactive |

As can be seen, each of those compounds with increased activity (as compared to its racemate) have the same absolute stereochemical configuration. For these measured compounds on NCIH2405 cells, those with structures of formula (Id) have increased measured activity. Moreover, as can be seen, in FIGS. 2A and 2B, racemic mixtures of these compounds also possess activity.

Example 5: Linker Containing Analogs for Chemo-Proteomic Target Identification

Linkered analogs useful for proteomic target identification were synthesized. One of these was synthesized according to the following schema:

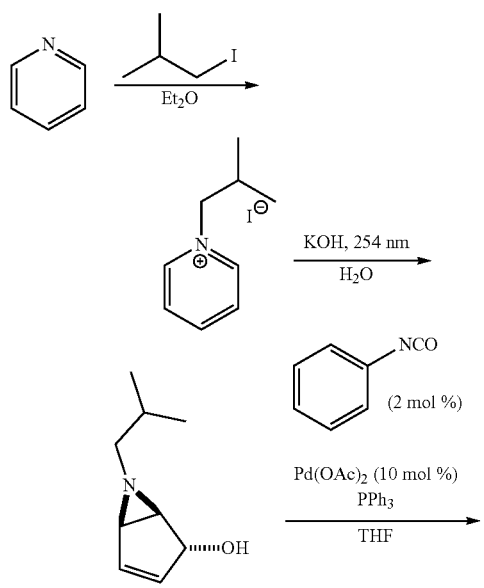

Another linkered compound was synthesized according to the following scheme:

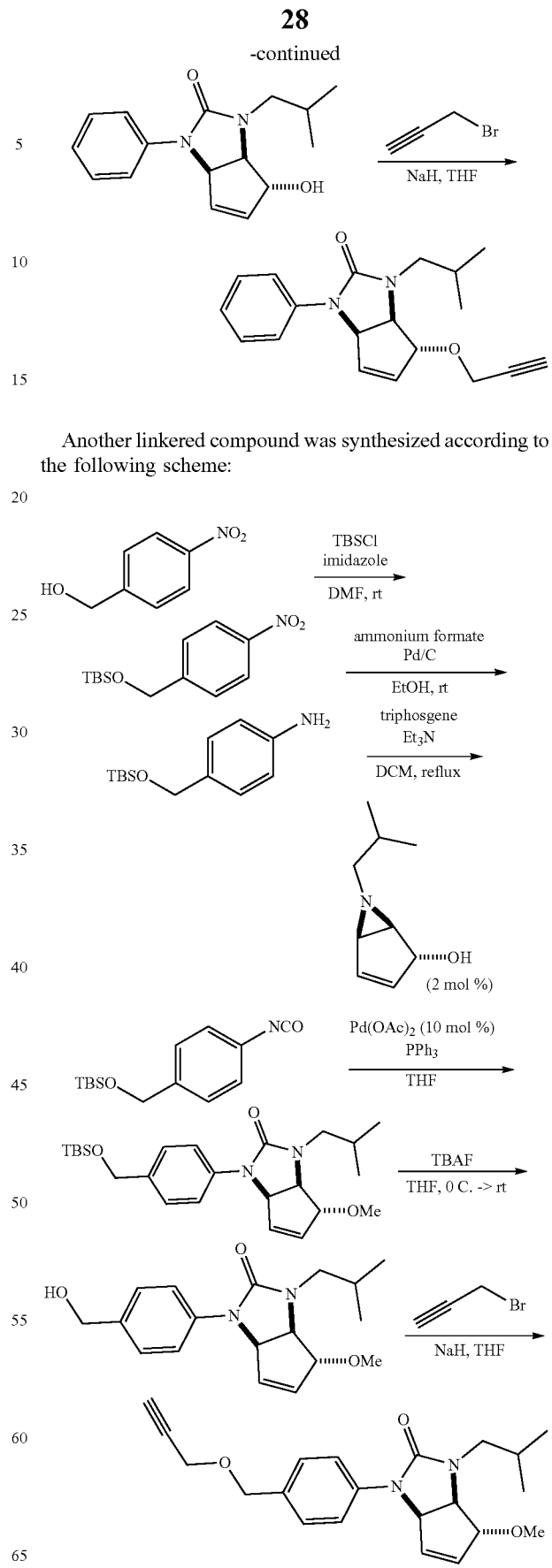

The linkered attachment is able to allow conjugation to other compounds such as biotin which may be useful in assays, mass spectrometric analysis, and other pulldown experiments.

The response to dose of several compounds (including a linkered analog) on PF0071 organoids were run. Enantiomers of E1, E5, and E8 were tested and compared to results with a linked compound synthesized as a racemic mixture as described above (identified in FIG. 3 as "Linked E1(Rac)") having the structure:

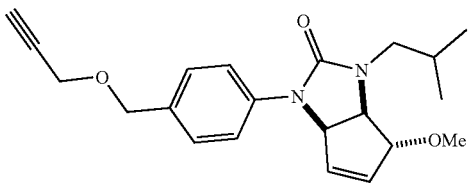

Figure 3:
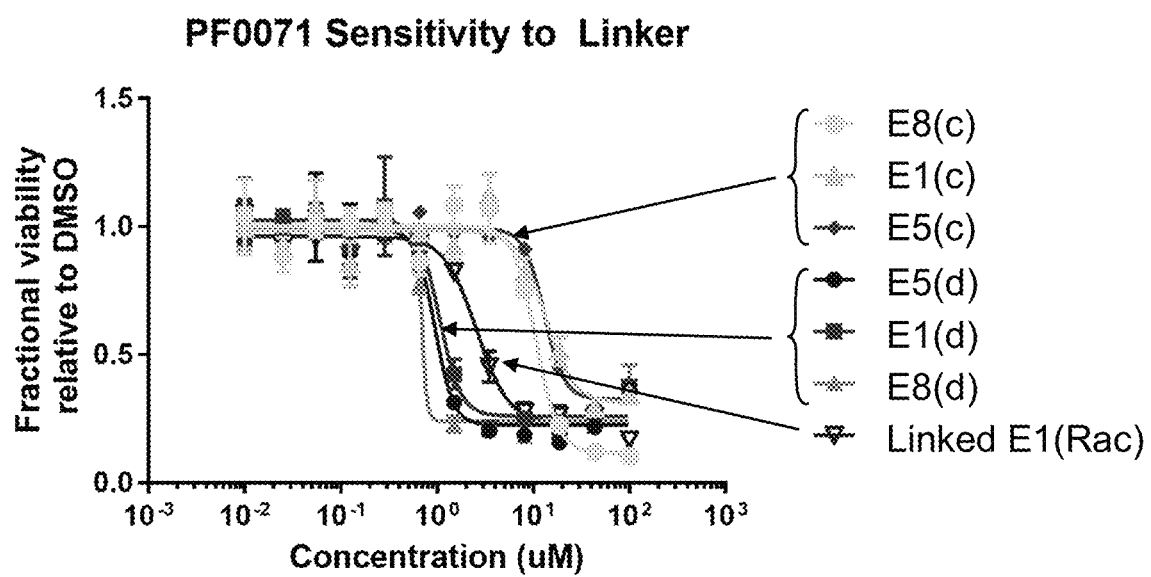
FIG. 3 shows the viability of the PF0071 organoid with respect to various compounds of the invention, including an analog of E1 comprising a moiety capable of being used as a linker.

FIG. 3 illustrates the dose response of these compounds to the organoid PF0071. As can be seen, compounds comprising a linking moiety have minimal or no loss of activity as compared to their non-linkered counterpart.

Example 6: Drug Metabolism and Pharmacokinetics (DMPK)

DMPK assays were performed on four compounds having the structure of formula (I(d)). Specifically, E1(d), E8(d) (labeled in FIGS. 4-5 as "chloro"), E11(d) (labeled in FIGS. 4-5 as "fluoro"), and E5(d) (labeled in FIGS. 4-5 as "reduced") were all compared with several standard drugs such as diethylstilbesterol, haloperidol, furosemide, and others.

Figure 4A:
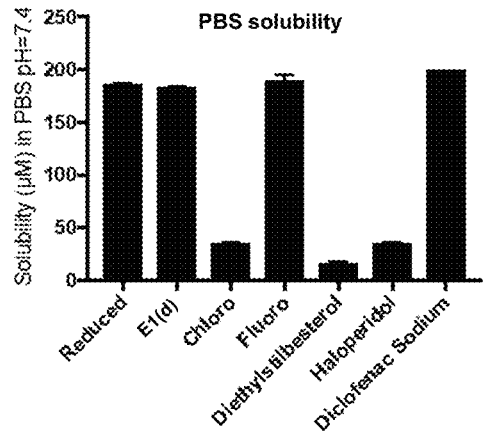
FIG. 4A shows the solubility of several compounds and standards in a PBS solution.
Figure 4B:
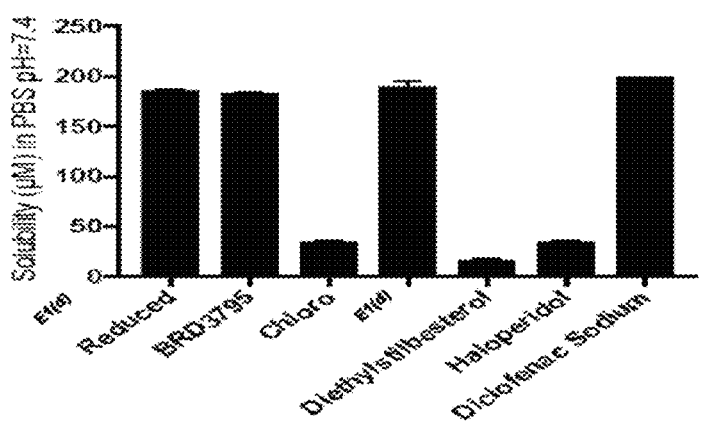
FIG. 4B shows the permeability of several compounds and standards across Caco-2 cells.
Figure 5A:
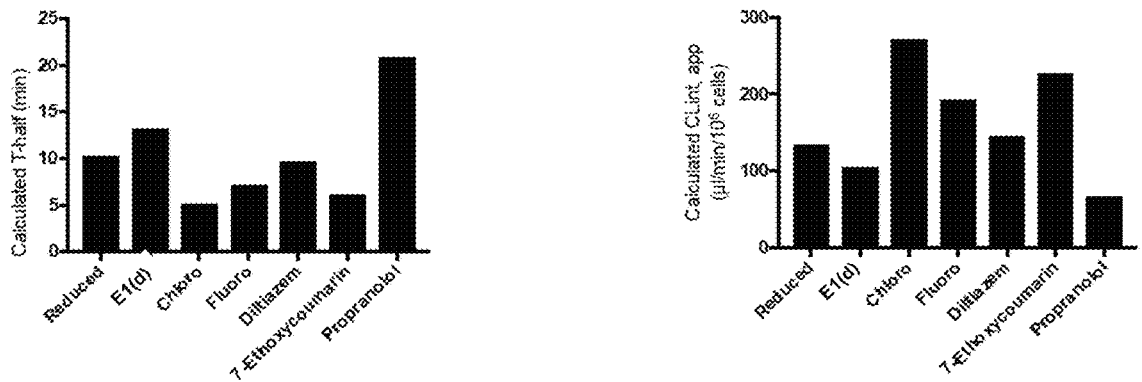
FIG. 5A illustrates the half-life (left) and clearance (right) of several test compounds and standards in mouse liver microsomes.
Figure 5B:
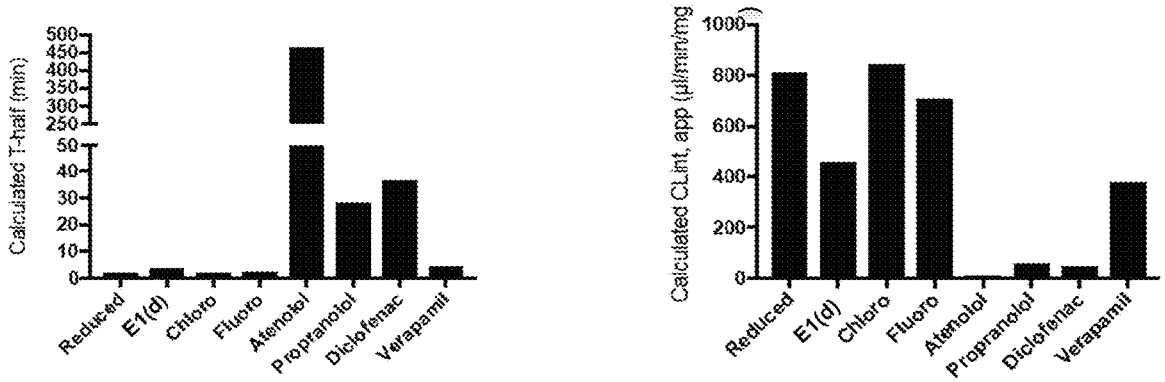
FIG. 5B shows the half-life (left) and clearance (right) of several test compounds and standards in mouse hepatocytes. In these figures, "reduced," "chloro", and "fluoro" refer to reduced (E5(d)), para-chlorinated on the $R_2$ phenyl (E8(d)), and para-fluorinated on the $R_2$ phenyl (E11 (d)) analogs of compound E1(d), respectively.

The kinetic solubility was measured with UV-Visible absorption (Spectrophotometer was Spectramax M5) at a test concentration of 200 µM (1% (vol/vol) DMSO) in phosphate buffered saline ("PBS") at pH 7.4. The solution was incubated for 2 hours at 25° C. with shaking. The measured absorbance was compared to a five-point linear calibration curve (2.5 to 200 µM, n=1) calibrated using liquid chromatography tandem mass spectrometry "LC-MS/MS"). The measured solubilities of these compounds is shown in FIG. 4A.

To investigate the intestinal permeability and drug efflux of various drugs, a Caco-2 permeability assay was run on the compounds as compared to several standards. Briefly, 2 µM (n=2) solutions were prepared in Hanks' Balanced Salt Solution (HBSS) with 10 mM HEPES. Caco-2 cells were allowed to grow for 10 days to produce $18.75 \times 10^3$ cells/well. Solutions were applied apically and allowed to permeate to basal cells (A to B) or applied basally and allowed to permeate to apical cells. Permeation occurred for 2.5 hours at 37° C., 5% $CO_2$, and 95% RH. The permeability coefficients (determined with liquid chromatography tandem mass spectrometry "LC-MS/MS") for several compounds and standards were determined and shown in FIG. 4B.

Figure 4C:
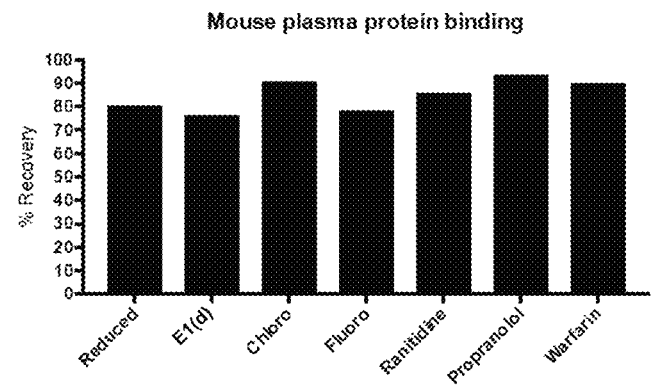
FIG. 4C shows the percent of test compound and standards recovered in a mouse plasma protein binding assay.

The mouse plasma protein binding was determined for several test compounds and standards on pooled mouse plasma using equilibrium dialysis. 1 µM concentrations were measured and left for 6 hours to reach equilibrium across the membrane in 37° C., 5% $CO_2$, 95% Relative Humidity environment. The measured % recovery (measured with LC-MS/MS) as compared to the original concentration values for the test compounds is shown in FIG. 4C.

Figure 4D:
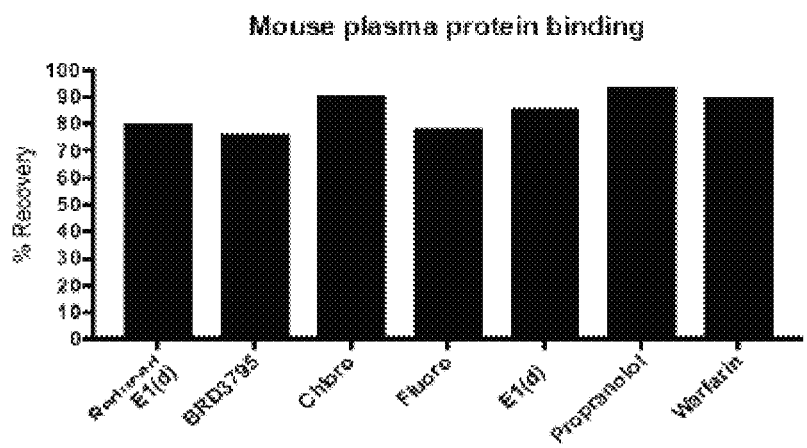
FIG. 4D shows the percent of test compounds and standards remaining after 60 minutes (black, left portion) and 120 minutes (grey, right portion) of incubation with mouse plasma protein. In these figures, "reduced", "chloro", and "fluoro" refer to reduced (E5(d)), para-chlorinated on the $R_2$ phenyl (E8 (d)), and para-fluorinated on the $R_2$ phenyl (E11(d)) analogs of compound E1(d).

The plasma protein stability of several compounds was also performed on pooled mouse plasma. Solutions of 2 µM were mixed with plasma and incubated at 37° C. (5% $CO_2$, 95% Relative Humidity) for up to two hours (0, 60 and 120 minutes). The % remaining (measured with LC-MS/MS) is shown in FIG. 4D.

The mouse liver microsome stability was also measured in 0.4 mg/mL mouse liver microsomes. Solutions of 1 µM were prepared and mixed with the microsomes (N=2). The mixture was incubated at 0, 5, 10, 20, 30, and 60 minutes with nicotinamide adenine dinucleotide phosphate regenerating system (NADPH/NRS) at 37° C. The half-life (left on FIG. 5A) and clearance (right on FIG. 5A) were determined for this system and compared to standards based on LC-MS/MS measurements.

Hepatocyte stability was also determined in cryopreserved pooled mouse hepatocytes. Cells were grown (0.5× $10^6$ cells/ml) in KHB supplemented with CaCl2, HEPES, fructose, glycine at pH 7.4. 1 µM solutions with the test compound or standards were mixed and incubated for 0, 15, 30, 45, 60, and 75 minutes at 37° C. (5% $CO_2$, 95% Relative Humidity) to determine the half-life (left on FIG. 5B) and clearance (right on FIG. 5B) using LC-MS/MS.

As can be seen in FIGS. 4 and 5, compounds having the structure of formula I (and particularly, compounds having the structure of formula I(d)) exhibit good solubility, plasma stability, permeability, and mouse plasma protein binding. However, these compounds exhibited low microsome and hepatocyte stability.

Other Embodiments

The disclosures of each and every patent, patent application, and publication cited herein are hereby incorporated herein by reference in their entirety.

While the disclosure provides specific embodiments, it will be understood that it is capable of further modifications and this application is intended to cover any variations, uses, or adaptations of the following, in general, the principles described herein and including such departures from the present disclosure come within known or customary practice within the art to which the disclosure pertains and may be applied to the essential features hereinbefore set forth.

The invention claimed is:

1. A compound having the structure of formula (I):

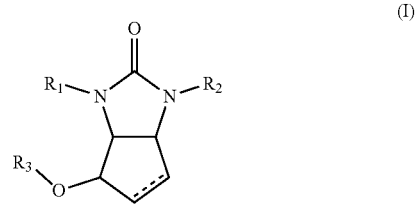

(I)

wherein the "dashed" bond (- -) is a single or double bond;

$R_1$ is optionally substituted $C_{1-6}$ alkyl;

$R_2$ is $C_{6-12}$ aryl or $C_{7-13}$ arylalkyl optionally substituted one to three times with halogen, —R, —OR, —(CH$_2$OCH$_2$)$_m$—(CH$_2$)$_p$—N$_3$, —(CH$_2$CH$_2$O)$_n$—(CH$_2$)$_p$—N$_3$, —CN, or combinations thereof;

$R_3$ is hydrogen, optionally substituted $C_{1-6}$ alkyl, —(CH$_2$OCH$_2$)$_m$—(CH$_2$)$_p$—N$_3$, or —(CH$_2$CH$_2$O)$_n$—(CH$_2$)$_p$—N$_3$;

R is independently at each occurrence optionally substituted $C_{1-6}$ alkyl; and m is independently selected at each occurrence from 0-5 and p is independently selected at each occurrence from 0-5;

or a pharmaceutically acceptable salt thereof.

2. The compound according to claim 1 having the structure of formula (Ia) or formula (Ib) or formula (Id):

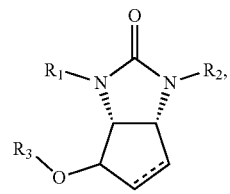

(Ia)

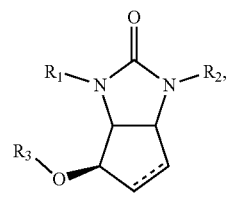

(Ib)

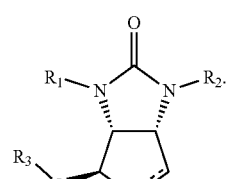

(Id)

3. The compound according to claim 1, wherein $R_1$ is $C_4$ alkyl.

4. The compound according to claim 1, wherein $R_2$ is phenyl or benzyl optionally substituted once with —F, —Cl, —CN, —CH$_3$, or —OCH$_3$.

5. The compound according to claim 1 wherein $R_3$ is hydrogen, methyl, or ethyl.

6. The compound according to claim 1, wherein the "dashed" bond is a double bond.

7. The compound according to claim 1, wherein the compound is selected from:

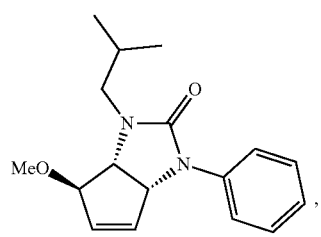

E1(d)

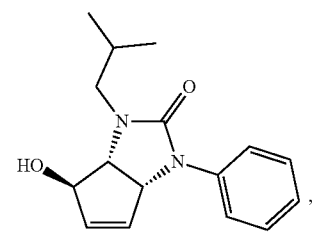

E2(d)

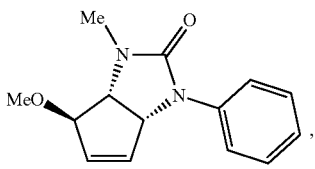

E3(d)

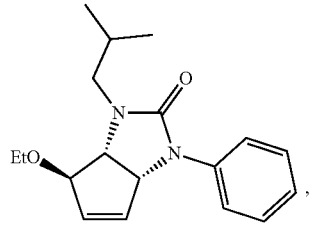

E4(d)

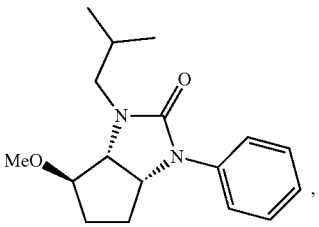

E5(d)

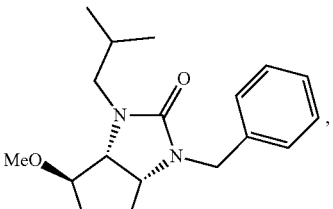

E6(d)

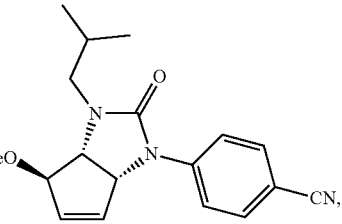

E7(d)

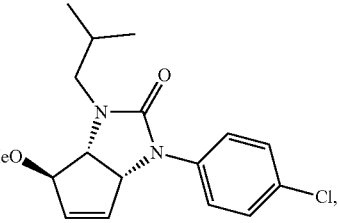

E8(d)

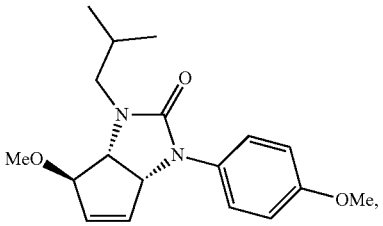

E9(d)

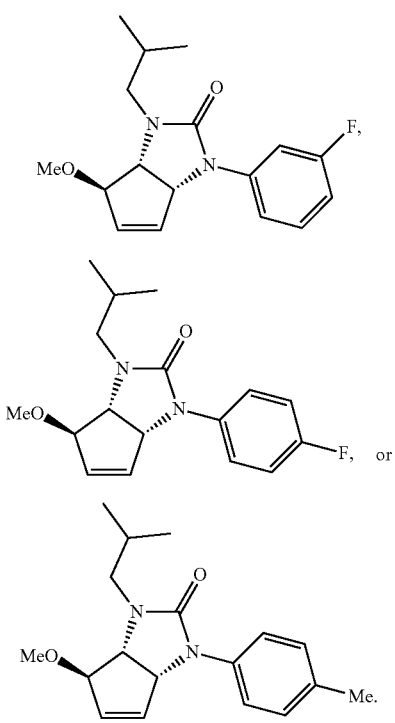

8. A pharmaceutical composition comprising the compound according to claim 1 and a pharmaceutically acceptable carrier, excipient, and/or diluent.

9. A method of killing a cancer cell comprising contacting said cancer cell with a compound according to claim 1.

10. The method according to claim 9, wherein said cancer cell is in vitro or in vivo.

11. A method of treatment of cancer comprising administering an effective amount of the compound according to claim 1 to a subject in need thereof, wherein the cancer is melanoma, gastrointestinal stromal tumors, lung cancer, skin cancer, colorectal cancer, breast cancer, prostate cancer, ovarian cancer, thyroid cancer, hematological malignancy, papillary thyroid carcinoma, cholangiocarcinoma, metastatic melanoma, glioblastoma multiform, pancreatic cancer, or acute myelogenous leukemia.

12. The method according to claim 11, wherein said cancer is pancreatic cancer.

13. The method according to claim 11, wherein said compound is coadministered with another anticancer agent.

14. The method according to claim 13, wherein said anticancer agent is vemurafenib or a pharmaceutically acceptable salt thereof.

15. The method according to claim 13, wherein said anticancer agent is a MEK inhibitor.

16. The method according to claim 15, wherein said MEK inhibitor is selected from trametinib, cobimetinib, selumetinib, binimetinib, or pharmaceutically acceptable salts thereof.

17. The method according to claim 11, wherein said compound is administered intravenously, intramuscularly, subcutaneously, topically, orally, intraperitoneally, intraorbitally, by implantation, by inhalation, intrathecally, intraventricularly, or intranasally.

* * * * *